United States Patent [19]

Kelly et al.

[11] Patent Number: 4,539,559
[45] Date of Patent: Sep. 3, 1985

[54] PORTABLE, DISPOSABLE WARNING DEVICE FOR DETECTING URINE-WET UNDERGARMENTS

[76] Inventors: Hugh Kelly, 737 Point Rd., Little Silver, N.J. 07739; Alvin Krass, 205 Holland Rd., Holmdel, N.J. 07701

[21] Appl. No.: 363,049

[22] Filed: Mar. 29, 1982

[51] Int. Cl.³ .............................................. G08B 21/00
[52] U.S. Cl. .............................. 340/573; 128/138 A; 200/61.05; 340/604
[58] Field of Search ............................. 340/573, 604; 128/138 A; 200/61.05, DIG. 2

[56] References Cited

U.S. PATENT DOCUMENTS

| | | | |
|---|---|---|---|
| 3,530,855 | 9/1980 | Balding | 128/138 |
| 3,696,357 | 10/1972 | Kilgore | 340/573 |
| 4,069,817 | 1/1978 | Fenole et al. | 340/573 |

Primary Examiner—Glen R. Swann, III
Attorney, Agent, or Firm—Armstrong, Nikaido, Marmelstein & Kubovcik

[57] ABSTRACT

A portable device for detecting when undergarments are wet with urine comprises electronic disposable sensor means in contact with said undergarment, an electronic detector means activated by said sensor means, and an alarm means activated by the detector means, all chosen and constructed such that there is no energization of any part of the system until a wet condition is detected and such that there is no possibility of more than 9 volts of electric potential in contact with the human body, with the current generated by said potential not to exceed 10 microamperes.

7 Claims, 5 Drawing Figures

PORTABLE, DISPOSABLE WARNING DEVICE FOR DETECTING URINE-WET UNDERGARMENTS

BACKGROUND OF THE INVENTION

Bladder incontinence is of course endemic in the very young, cured only by intensive training as the human animal goes through its second and third year of life, and requiring the use, until then, of special undergarments (diapers). The same problem can affect the elderly or the infirm or persons of any age who have this problem because of either some physiological or neurological problem or because of a psychological one. This problem may be a major source of embarrassment. The mere fear of such incontinence can be a danger to the psychological welfare of persons already subject to severe psychological pressures due to other infirmities. Such people, both the very young and the infirm often have no warning that their undergarments are being wet by urine until they are uncomfortably wet, yet often there is some gradual leakage in advance of such a state. There is a need for a device which can warn the person involved, or his caretaker (nurse or parent) that such leakage is occurring.

A signalling device can serve to condition the wearer to obtain better bladder control, and may result in improved attitudes and state of psychological wellbeing. Other advantages of improved sanitary and esthetic states are significant, also.

Urine, of course, is a solution of among other things, electrolytes, and will conduct a current of electricity. However, there are serious dangers involved in the use of electrical devices which use this property to sound an alarm. Fail-safe circuitry is a positive must, else there is serious danger of bodily harm. Further, the device to be portable must be capable of operation for the maximum life of the battery.

SUMMARY OF THE INVENTION

We have found a device which solves the above problems in a unique way, comprising a disposable sensor unit, a portable detector unit and signalling unit, in combination. These units are described and characterized more fully in the following discussion.

This invention relates to a portable electronic device for producing a signal when an undergarment is wet with urine. More specifically, it relates to a device which comprises in combination a disposable sensor circuit, an oscillating means and an indicating means, in which the sensor circuit comprises:

(i) Separated electric terminals mounted or printed on a disposable pad to facilitate contact with an undergarment, (ii) conducting leads from said terminals, (iii) said leads being connected through a voltage source and a resistance means, (iv) said resistance means having a resistance value at least ten times the resistance to be expected between said terminals when the latter are in contact with an undergarment wet with urine, and (v) the voltage from said voltage source and the resistance in said resistance means are chosen such that, in combination with the resistance between said terminals, the current flow does not exceed ten microamperes.

BRIEF DESCRIPTION OF THE DRAWINGS

This invention can be more fully understood in relation to the accompanying drawings which show in detail a preferred embodiment.

In the drawings

DESCRIPTION OF THE PREFERRED EMBODIMENT

Figure 1:
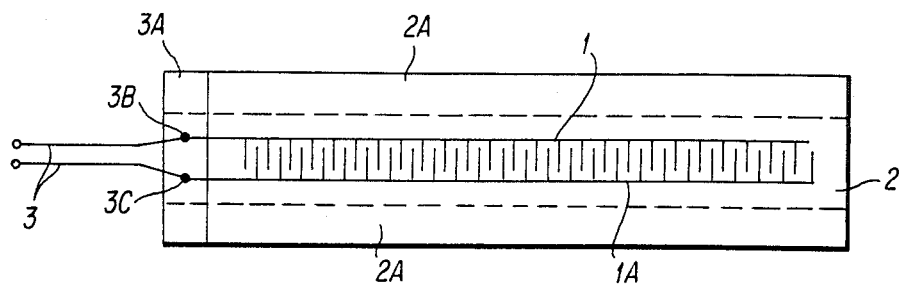
FIG. 1 is a schematic top plan view of the disposable part of a preferred sensor unit.

More specifically, in the sensor unit shown in FIG. 1, electrodes 1 and 1A are printed on a flexible absorbant pad 2, preferably with a separation of two to five millimeters. Pad 2 also has a backing of two adhesive strips 2A for fastening it to sheets or diapers or undergarments. The adhesive backing 2A can be in any other configuration found convenient. A flexible two-wire cord 3 is attached to a clamp or pin 3A having electrical connection 3B and 3C attached to the separate wires of cord 3. Clamp 3A is fastened to the disposable pad 2 in any convenient way and electrodes 1 and 1A are fastened to connectors 3B and 3C, thus becoming connected electrically to the rest of the sensor circuit through cord 3.

Figure 2:
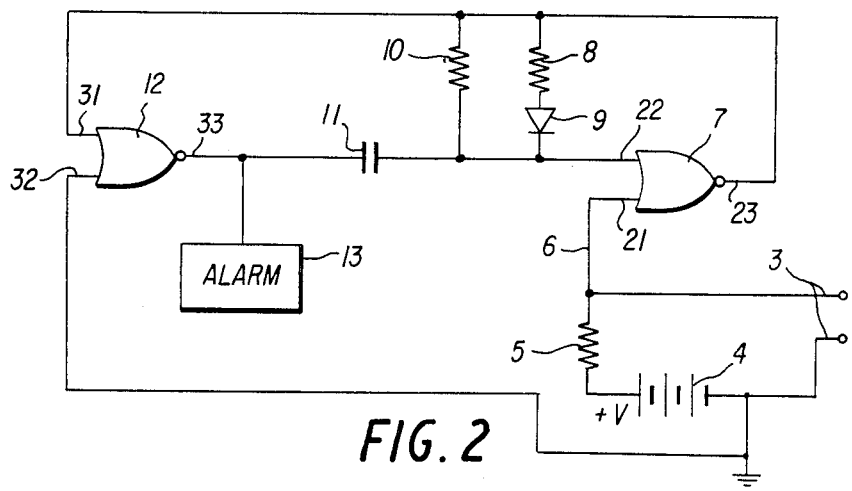
FIG. 2 is a schematic electronic wiring diagram of a preferred detector unit connected to the rest of the said sensor unit.

The flexible cord 3 leads to the compact, portable detector and alarm units which are housed in the same container (not shown) together with the rest of the sensor means circuitry 3, 4, and 5, shown in FIG. 2, in which a battery 4 with a potential of V volts and a resistor 5 complete the sensor circuit. This circuit is connected electrically by lead 6 to the detector means into input lead 21 of CMOS NOR gate 7. The input lead 22 and output lead 23 of said gate 7 are part of the detector unit which is oscillatory when the input lead 21 of gate 7 is near zero volts and quiescent or non-oscillatory when the input lead 21 of gate 7 is near +V volts.

The remainder of the oscillator unit which comprises the detector means connects output lead 23 of gate 7 through a resistor 8 and a diode 9 in parallel with a larger resistor 10 to input lead 22 of gate 7. The remainder of the oscillator unit also comprises a capacitor 11 and leads 31 and 33 of a second CMOS NOR gate 12. Lead 32 of gate 12 is connected to the grounded terminal of battery 4. The detector means is connected, between output lead 33 of gate 12 and capacitor 11 to the alarm means 13.

Figure 4:
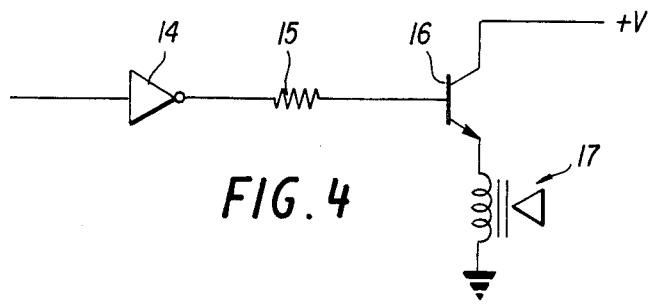
FIG. 4 is an electronic schematic wiring diagram of a preferred embodiment of said alarm means.

The alarm means (FIG. 4) in turn comprises an electrical connection through an invertor 14 and a resistor 15 to the base of transistor 16 whose collector is connected to +V of battery 4. The emitter of transistor 16 is connected to speaker 17, which is in turn connected to ground. When activated by transistor 16, speaker 17 sounds an audible alarm.

In the operation of the device described in the drawing, the sensor means pad 2 is affixed to the undergarment or to a disposable diaper with the printed electrodes in contact with them and with the detector unit via connectors 3B and 3C, FIG. 1, and the flexible cord 3—FIG. 1. The rest of the unit, conveniently boxed in a container is either hung on a belt, put in a pocket or otherwise unobtrusively stowed. Under dry conditions the resistance between the electrodes in the printed circuit 1 and 1 A is very high—over 10 megohms. However, should the undergarment in contact with electrodes 1 and 1 A become wet with urine, this will fall to values below 0.1 megohms. The size of resistor 5 is carefully chosen such that in combination with battery 4 (usually 9 volts), a current of less than 10 microamperes will flow in the sensor circuit. A value for resistor 5 of at least 10 times the maximum expected resistance between electrodes 1 and 1 A under wet conditions will guarantee such maximum and therefore safe current.

The detector means is designed to detect the flow of current in the sensor means circuit and transform it into an oscillation to activate the alarm means. It is further designed to be quiescent until such current flows and therefore to provide no drain on battery 4 until then.

In the quiescent (dry) state, the voltage at input lead 21 of gate 7 is near +V, the voltage of battery 4, and the voltage at output lead 23 and input lead 22 of gate 7 and input lead 31 of gate 12 is near zero. Output lead 33 of gate 12 is near +V. Capacitor 11 is therefore charged with nearly +V at the plate connected to output lead 33 of gate 12, and nearly zero at the plate connected to input lead 22 of gate 7. When the sensor becomes "wet", the voltage at input lead 21 of gate 7 drops to nearly zero volts. Since input lead 22 of gate 7 was nearly zero volts, this change causes output lead 23 of gate 7 and input lead 31 of gate 12 to change from nearly zero to nearly +V and output lead 33 of gate 12, to change from nearly +V to near zero. Capacitor 11 then changes toward nearly +V on the plate attached to input lead 22 of gate 7. The rate of charging (time constant) is determined by the value of capacitor 11, resistors 8 and 10 and the forward resistance of diode 9. Since resistor 8 is much smaller than resistor 10 and the resistance of forward biased diode 9 is low, the time constant is essentially determined by capacitor 11 and resistor 8. As the potential on input lead 22 of gate 7 approaches +V, the gate turns "off" and the voltage at output lead 23 of gate 7 and input lead 31 of gate 12 goes to nearly zero volts. This turns "on" gate 12 and output lead 33 of gate 12 goes to nearly +V. Capacitor 11 then changes toward +V on the plate attached to output lead 33 of gate 12 and zero volts on the plate attached to input lead 22 of gate 7. The diode 9 is reverse biased at this time and the changing rate is determined by the value of capacitor 11 and resistor 10. When input lead 22 of gate 7 approaches zero volts the gate turns "on" and the cycle repeats as long as a wet condition maintains flow in the sensor circuit.

Figure 3:
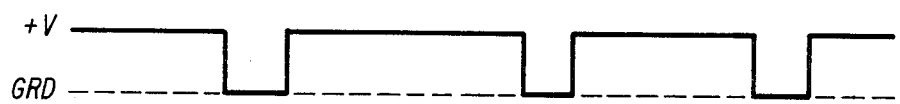
FIG. 3 is a drawing of the wave emission supplied to the alarm means by said detector unit.

The relative times of the oscillation between ground and full voltage at output lead 33 of gate 12 is controlled by the relative sizes of resistors 8 and 10 and of capacitor 11 with the wave form shown in FIG. 3 being produced. The time at full voltage is a function of resistor 10 and capacitor 11 and the time at ground a function of resistor 8. To keep current drains to a minimum, resistor 10 is chosen to provide a time constant of 1 second and resistor 8 provides a time constant of 5 milliseconds. Since the alarm will be energized only when resistor 8 is controlling, the results will be a series of clicks, about one second apart.

The voltage at input lead 21 of gate 7 determines whether the circuit is quiescent or oscillating. This is controlled by the voltage of the battery 4, the value of resistor 5 and the resistance between electrodes 1 and 1 A. Resistor 5 is chosen as 1 megohm to limit to less than 10 microamperes. However, under "dry" conditions between electrodes 1 and 1 A, the voltage output lead 33 of gate 12 is held at nearly the full output of battery 4. Under "wet" conditions the voltage at output lead 33 of gate 12 drops to almost ground, and the circuit oscillates.

Oscillating signal is transmitted to the alarm means through an inverter 14 in order to maintain the zero current flow in transistor 16 in the quiescent stage. What is wanted is a sounding of an alarm during the time when the detector circuitry is near ground at input lead 21 of gate 7, since this occurs only when current is flowing in the sensor unit. Inverter 14 reverses the wave form to maintain ground at base of transistor 16 until current flows in the sensor circuit and activates the oscillation of the detector circuit. Resistor 15 functions to control the amplitude of the current applied to the speaker. If resistor 15 is 6000 ohms, a current of about 100 microamperes is applied to speaker 17 for about 5 milliseconds every 1 second.

Many variations in the construction of the device of this invention will be readily apparent. The electrodes which detect the urine-wet condition of the undergarment could be separately mounted or even be a part of the structure of the undergarment itself, either by printed circuits on the cloth or by electrodes sewn into the garment. The further apart they are, the more the garment will have to be wet before detection occurs and the greater the resistance to electric current flow between them, which in turn will require modification of resistor 5 to get the proper current values. It is important that no more than about 10 microamperes of current be possible in the sensor circuit, in order to guarantee against danger to the wearer.

The detector or circuitry shown in the drawing is a standard well known oscillating circuit. Any oscillating circuit which will remain quiescent until energized by flow of current in the sensor circuit and which will activate an alarm signal when energized is usable.

Figure 2A:
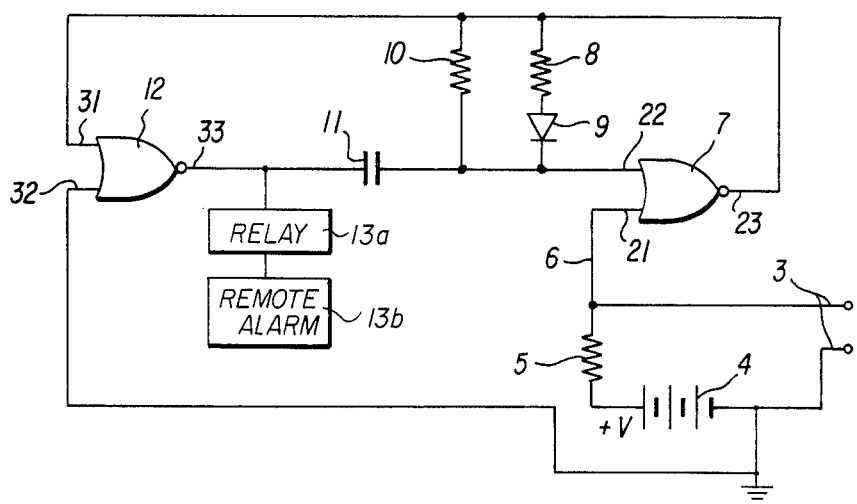
FIG. 2a is a schematic diagram of an alternate embodiment of the detector unit.

The alarm shown in the drawings is a small audible speaker, emitting only a few faint clicks, audible only to the wearer in order to reduce embarrassment. However, depending on the circumstances of use, many other signals can be envisaged. If the patient is bedridden, there may be a need for a more audible or more easily detected signal such as a light. The alarm means could be a remote unit 13b (see FIG. 2a) set off by radio waves, energized by relay 13a, or via wires activated by the detector unit being energized. Such a unit would be important for remote control in a hospital to prevent bed sores.

The undergarment whose dryness is to be monitored need not be an ordinary undergarment. It can also be a special undergarment designed for protection against bladder incontinence, such as a diaper. While the use of the device of this invention on small babies is not, under normal conditions, contemplated, one can envisage special situations in which it could be useful. Certainly, as children grow older and are being trained, a device of this sort could have very practical uses. However, its primary use is envisaged as a monitor in hospital care and as a psychological guard for those who are having control problems.

We claim:

1. A portable electronic device with a disposable sensor for producing a signal when an undergarment is wet with urine, which comprises, in combination
    (a) a sensor circuit comprising
        (i) separated electric terminals mounted to facilitate contact with said undergarment,
        (ii) conducting leads connected to said terminals,
        (iii) said leads being connected together through a voltage source and a resistance means,
        (iv) said resistance means having a resistance value at least ten times the resistance to be expected between said terminals when in contact with said urine-wet undergarment,
        (v) the voltage from said voltage source and the resistance in said resistance means being chosen such that, in combination with the resistance between said terminals, no more than 10 microamperes of current can flow in said sensor circuit;
    (b) an oscillating means connected to said sensor circuit in such manner that said oscillating means oscillates only when current passes in said sensor circuit, and
    (c) an indicating means connected through an inverting means to said oscillating means.

2. The device of claim 1 in which the said sensor circuit separated terminals comprise electrodes printed on a small absorbent pad with adhesive backing.

3. The device of claim 2 in which the said electrodes have a separation of between 2 and 5 millimeters.

4. The device of claim 3 in which said voltage source is a 9 Volt battery and said resistance means has a value of 1 megohm.

5. The device of claim 4 in which the said oscillating means is a CMOS astable oscillator connected to said sensor circuit through the control lead of a CMOS NOR gate.

6. The device of claim 5 in which the said indicating means is a sound generating device.

7. The device of claim 5 in which the said indicating means comprises a relay activating a remote indicating means.

* * * * *